United States Patent
Sirdesai et al.

(12) 
(10) Patent No.: US 6,244,274 B1
(45) Date of Patent: Jun. 12, 2001

(54) THIXOTROPIC POLYMERIZABLE NAIL SCULPTING COMPOSITIONS

(75) Inventors: Sunil J. Sirdesai, Irvine; George Schaeffer, Beverly Hills, both of CA (US)

(73) Assignee: OPI Products, Inc., North Hollywood, CA (US)

( * ) Notice: Subject to any disclaimer, the term of this patent is extended or adjusted under 35 U.S.C. 154(b) by 0 days.

(21) Appl. No.: 09/365,344

(22) Filed: Jul. 30, 1999

(51) Int. Cl.$^7$ .................................................. A45D 31/00
(52) U.S. Cl. .............................................. 132/200; 132/73
(58) Field of Search ................. 132/200, 73, 285

(56) References Cited

U.S. PATENT DOCUMENTS

| | | |
|---|---|---|
| 3,782,961 | 1/1974 | Takahashi et al. . |
| 3,829,531 | 8/1974 | Graff . |
| 3,850,770 | 11/1974 | Juna et al. . |
| 3,864,133 | 2/1975 | Hisamatsu et al. . |
| 3,891,523 | 6/1975 | Hisamatsu et al. . |
| 3,895,171 | 7/1975 | Deamud et al. . |
| 3,899,611 | 8/1975 | Hall . |
| 3,907,574 | 9/1975 | Yonezawa et al. . |
| 3,912,516 | 10/1975 | Recchia et al. . |
| 3,928,113 * | 12/1975 | Rosenberg ............................. 132/73 |
| 3,932,356 | 1/1976 | Takagi . |
| 3,989,609 | 11/1976 | Brack . |
| 4,129,667 | 12/1978 | Lorenz et al. . |
| 4,135,007 | 1/1979 | Lorenz et al. . |
| 4,171,979 | 10/1979 | Novak et al. . |
| 4,333,998 | 6/1982 | Leszyk . |
| 4,374,237 * | 2/1983 | Berger et al. ........................ 528/28 |
| 4,690,369 * | 9/1987 | Giuliano ................................ 132/73 |
| 4,881,974 | 11/1989 | Herrington . |
| 4,929,403 * | 5/1990 | Audsley ................................ 264/22 |
| 5,066,621 | 11/1991 | Akhtar . |
| 5,084,421 | 1/1992 | Herrington . |
| 5,127,414 * | 7/1992 | Mast et al. ............................ 132/73 |
| 5,146,531 * | 9/1992 | Shustack ............................. 385/128 |
| 5,385,966 | 1/1995 | Hermansen et al. . |
| 5,444,108 | 8/1995 | Hagquist et al. . |
| 5,521,232 | 5/1996 | Gynn et al. . |
| 5,554,684 | 9/1996 | Choi et al. . |
| 5,571,570 | 11/1996 | Lake . |
| 5,927,293 * | 7/1999 | Halpern .............................. 132/73 |

* cited by examiner

Primary Examiner—Todd E. Manahan
(74) Attorney, Agent, or Firm—Blakely, Sokoloff, Taylor & Zafman LLP

(57) ABSTRACT

A polymerizable thixotropic oligomeric composition for sculpting artificial fingernails which is non-yellowing, and which maintains its shaped when formed and polymerizes rapidly under actinic radiation.

11 Claims, 1 Drawing Sheet

THIXOTROPIC POLYMERIZABLE NAIL SCULPTING COMPOSITIONS

FIELD OF THE INVENTION

The invention relates to artificial nail structures and protective coatings for use on human nails.

BACKGROUND OF THE INVENTION

Artificial fingernails are generally prepared by a two-part powder/liquid system. It is known to the art in fingernail industry that traditional acrylic coatings from powder and liquid monomers have significant disadvantages. The powder formulated with a catalyst and the liquid monomer formulated with a co-catalyst (typically an amine) must be mixed at a particular concentration level in order to be applied to the fingernail. The procedure calls for the user (e.g., manicurist) to wet a brush with liquid monomer, retrieve the powder on the wet bristles and apply the coating to the fingernail. The coating dries into an artificial fingernail typically through a reduction-oxidation (redox) reaction.

In prior art two-part systems, the proportions of the ingredients are critical. Accordingly, conventionally cured acrylics lack a consistency generally required in professional industry. A second limitation of the two-part system is that the liquid monomers generally have strong unpleasant odors. Still another limitation of this system is the inherent property of discoloration, typically yellowing, of the artificial fingernail over a very short period of time. This discoloration occurs due to the presence of an amine as a co-catalyst in the liquid monomer. Manufacturers have attempted to mask the discoloration through the usage of dye in the liquid monomer. A variation of this system is to replace the amine co-catalyst with photoinitiator and cure the system with actinic radiation rather than curing by a redox mechanism. Though this addresses the discoloration problem, it is still a two-part system where one relies on the user (e.g., manicurist) to use the right ratio of ingredients.

Photo-curable oligomeric artificial fingernail coating compositions overcome several disadvantages discussed above with the traditional powder/liquid system. In particular, photo-curable oligomeric compositions are premixed by the manufacturer with the polymerization initiator, and not by the manicurist when the coating is to be applied to form an artificial fingernail. Thus, mixing and measurement errors can be avoided and a more consistent product can be obtained.

Despite their many advantages, photo-curable oligomeric coating compositions pose problems that need to be addressed before they became a serious challenger to the powder/liquid system that dominates the artificial fingernail arena of the beauty industry. Acrylic urethane oligomers blended with monomer(s), cross linker(s), and photoinitiator(s) are easy to apply to fingernails by a brushing technique. Once applied, these coatings are capable of leveling, and thereby minimizing surface irregularities or waviness, and develop the necessary appearance properties required of an artificial fingernail. However, the viscosity and thixotropic properties of these compositions are such that after application on fingernails they are prone to run and sag due to gravity. For the most part, these coatings have been used only as overlays over natural fingernails or artificial tips because of their excellent leveling properties. Their propensity to sag severely limits their application to sculpt free edges on the natural fingernail. A few products have been marketed to form or sculpt a free edge on the fingernail. In order to prevent sagging, the user (e.g., manicurists) must sculpt an individual fingernail and cure it before proceeding to sculpt the next fingernail. Any attempts made to sculpt all fingernails on one hand before curing resulted in these coatings failing to hold their shape due to various degrees of sagging. In spite of providing an odor free environment, sculpting and curing one fingernail at a time entails too much time and makes this process economically unfeasible for the user. Hence, improved flow control of these acrylic urethane oligomeric compositions is therefore critical to their ease of applications to sculpt free edges on natural fingernails that have complex surface contours.

Representative examples of prior photocurable coating compositions include those disclosed in U.S. Pat. Nos. 3,782,961, 3,829,531, 3,850,770, 3,864,133, 3,891,523, 3,895,171, 3,899,611, 3,907,574, 3,912,516, 3,932,356, 3,989,609, 4,129,667, 4,135,007, 4,171,979, 4,333,998, and 5,571,570. Most of these patents use volatile solvents as carriers that need to be evaporated to obtain the right consistency for spreading with a brush or spatula. Others need extreme measures like the use of 800 to 2000 watt high pressure mercury vapor lamps or electron beams for curing purposes. Needless to say, both these curing methods are extremely harsh to be used in the beauty industry.

Various thixotropic compositions have been developed for the coating industry but most of them are either two component systems or thermally curable. Representative examples of prior thixotropic coating compositions include those disclosed in U.S. Pat. Nos. 5,554,684, 5,521,232, 5,444,108, 5,385,966, 5,084,421, 5,066,621, and 4,881,974. The prior art does not reveal thixotropic compositions that have been developed for the fingernail care industry. Typically thixotropes used in the referenced patents include organoclays, castor oil, and filmed silica.

SUMMARY AND OBJECTS OF THE INVENTION

The invention relates to an improved photopolymeric one-part composition to sculpt artificial fingernails of a desired shape and length. The invention relates to photopolymeric compositions with improved flow control that can be applied to all five fingernails of one hand without sagging. After application, the fingernails with the coating composition may be exposed to actinic radiation for curing purposes. Besides their non-sagging properties, the compositions of the invention exhibit only slight leveling in localized areas of application, and hence need far less filing. The composition of the invention is non-toxic and is not a sensitizer.

The invention thus provides a photopolymerizable system that, with improved flow control characteristics, will promote ease of spreading with a brush and adequate leveling while inhibiting sagging and dripping. In an uncured condition, the system will not flow under small stresses such as those imposed by gravity acting on moderately thick layers of the coating composition but will flow readily when a low yield stress like brushing is exceeded so that application is facilitated. Such rheological behavior is termed thixotropy, and fluids that exhibit such behavior are said to be thixotropic.

The invention also provides fingernail enhancement products that will result in a substantial time savings for the user (e.g., manicurist) and greatly increase the ease with which artificial fingernails can be sculpted while providing an odor free environment.

DETAILED DESCRIPTION OF THE DRAWINGS

DETAILED DESCRIPTION OF THE INVENTION

Figure 1:
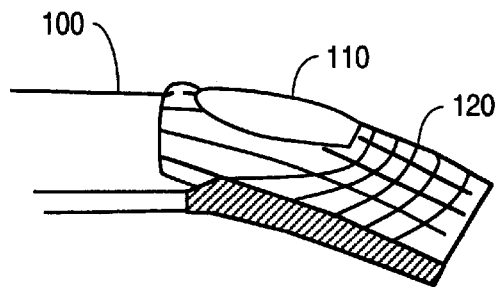
FIG. 1 is a side plan view illustration of a portion of a finger and a fingernail with a fingernail extension form applied to the finger.

This invention comprises photopolymeric compositions that are useful for fashioning artificial fingernails and/or decorative coatings in situ on a fingernail. In general, these compositions form a hard fused polymer when cured under actinic radiation in the shape of a fingernail. These compositions can be applied to all fingernails (e.g., five or ten fingers) prior to curing and they will not sag before they are cured, for example, under actinic radiation.

In one embodiment, the composition of invention is comprised of acrylated or methacrylated aliphatic urethane oligomer(s) blended with cross-linker(s) and/or monomer (s), thixotrope(s), initiator(s), inhibitor(s) and auxiliary components like pigments/dyes.

A representative structure of acrylated aliphatic urethane oligomer is shown below:

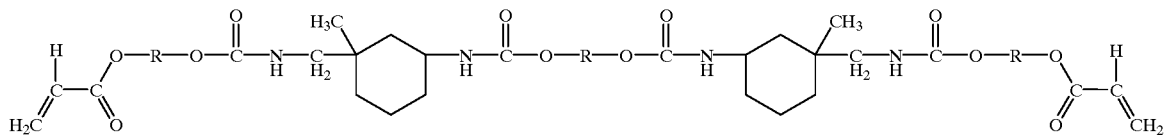

wherein Group R is an aliphatic hydrocarbon. Suitable constituents for Group R include, but are not limited to, $(CH_2)_n$, wherein n is 1–5.

Commercially available acrylic aliphatic urethanes suitable for use in the coating composition of the invention include but not limited to Echo Resin ALU 303, 304, 323, 350, 351, 352, 370, 371, 372, 373, 380, 381, 382, 383 (manufactured by Echo Resins of Versailles, Mo.), or Purelast 544, 546, 548, 569, 586, 590/A, 595/A, 597/A, 598/A (manufactured by Polymer Systems Corp. of Orlando, Fla.), and combinations thereof. In one embodiment, the resins are used in concentrations between 20% and 80% by weight of the total composition.

Cross-linkers used in the composition of the invention can be either bi-, tri- or multifunctional. Examples include, but are not limited to, triethylene glycol dimethacrylate (TEDMA), ethylene glycol dimethacrylate (EDMA), diethylene glycol dimethacrylate, tetraethylene glycol dimethacrylate, poly(ethylene glycol) dimethacrylate, 1,3-butanediol dimethacrylate, 1,3-butanediol dimethacrylate, 1,4-butanediol dimethacrylate, 1,6-hexanediol dimethacrylate, 1,12-dodecanediol dimethacrylate, neopentyl glycol dimethacrylate, trimethylolpropane trimethacrylate, and combinations thereof. In one embodiment, the cross-linkers are used in concentrations between 0% and 50% by weight of the total composition.

Certain monomers can also be added to the composition of the invention, if necessary, to achieve the desired properties. Examples of suitable monomers include, but are not limited to, hydroxyethyl methacrylate, hydroxypropyl methacrylate, isobornyl acrylate, methoxyethoxyethyl methacrylate, tetrahydrofurfuryl methacrylate, ethoxy ethyl methacrylate, ethoxyethoxyethyl methacrylate, benzyl methacrylate, phenethyl methacrylate, n-propyl methacrylate, isobutyl methacrylate, t-butyl methacrylate, n-butyl methacrylate, dimethyaminoethyl methacrylate, diethyleminoethyl methacrylate and combinations thereof. Preferrable monomers include hydroxymethyl methacrylate and/or isobomyl acrylate. Dimethyaminoethyl methacrylate or diethyleminoethyl methacrylate is used as the monomer, for example, when the actinic radiation used to cure the composition is visible light. Ethyl methacrylate can be used as the monomer, for example, if an odor free environment is not necessary.

The initiator that may be used in one embodiment of the composition of the invention include either visible or ultraviolet (UV) light initiators (e.g., photoinitiators) in concentrations between 1% and 7% by weight of total composition. One preferred concentration of initiator is in the range of 4%. Suitable photoinitiators include, but are not limited to, benzoin methyl ether, 2-hydroxy-2 methyl-1-phenyl-1 -propanone ("Darocur 1173"), camphorquinone, benzophenone, benzoin, benzoin-n-butyl ether, benzoin-isobutyl ether, propiophenone, acetophenone, methylphenylglyoxalate, 1-hydroxycyclohexyl phenyl ketone, 2,2-diethoxyacetophenone, ethylphenylpyloxylate, phenanthraquinone, and the like, and combinations thereof. One UV photoinitiator of choice is DAROCUR 1173™ and one visible photoinitiator is camphorquinone.

In one embodiment, the composition of the invention contains a thixotrope in an amount between 0.5% and 10% of the total composition. The thixotropes include, but are not limited to, an emulsion containing polyquaternium 37, propylene glycol dicaprylate/dicaprate, PPG-1 trideceth-6. These emulsions are sold by Ciba Specialty Chemicals Corp. of High Point, N.C. as SALCARE SC 95™ and SALCARE SC 96™ which may be used with or without fumed silica.

In addition to the above components, an embodiment of the photopolymeric composition of the invention may optionally contain a polymerization inhibitor such as butylated hydroxytoluene (BHT) or methyl ether of hydroquinone (MEHQ) to prevent premature reaction prior to use, to provide adequate long term stability, and to control the polymerization speed. Finally, auxiliary components like pigments and/or dyes may be included so as to modify color and final appearance of the artificial fingernail.

FIGS. 1–5 demonstrate the application of an embodiment of the composition of the invention to a fingernail. Initially, the surface of fingernail 110 of finger 100 is thoroughly cleaned by a volatile solvent which entails dehydrating fingernail 110. This is followed by priming the keratin surface of fingernail 110 with methacrylic acid or its homologues. Non-stick flexible form 120 is then inserted under the tip of fingernail 110 and extends out and with the same curvature as the natural fingernail.

Figure 2:
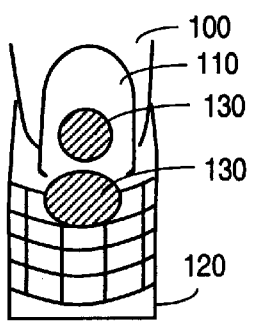
FIG. 2 is a top plan view of the finger and fingernail of FIG. 1 with two portions of the composition of the invention applied to the fingernail and the finernail extension form in accordance with an embodiment of the invention.
Figure 3:
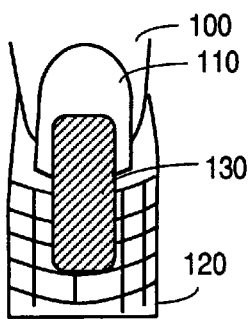
FIG. 3 is a top plan view of the finger and fingernail of FIG. 1 with the composition of the invention applied to a portion of the fingernail and the fingernail extension form in accordance with an embodiment of the invention.
Figure 4:
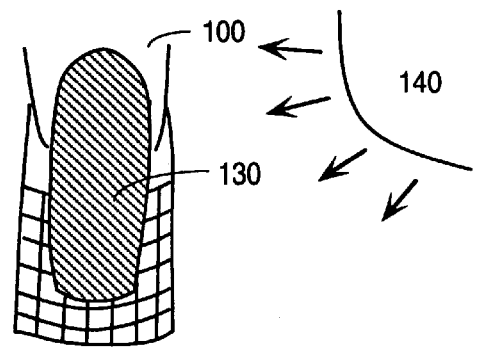
FIG. 4 is a top plan view of the finger and fingernail of FIG. 1 with the composition of the invention forming an artificial nail structure and being cured in accordance with an embodiment of the invention.

The composition of the invention is next applied at a desired thickness. FIG. 2 shows two portions of composition 130 applied to fingernail 110 and form 120, respectively. Composition 130 is formed and finished with the desired shape and length to form an artificial fingernail. FIGS. 3 shows the formation of a portion of an artificial fingernail. FIG. 4 shows the formation of a more substantial artificial fingernail covering the entire portion of nail 110 and extending beyond the end of nail 110.

Figure 5:
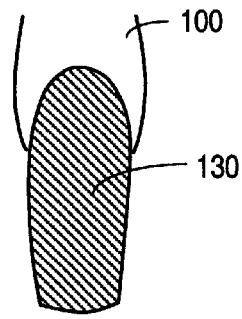
FIG. 5 is a top plan view of a portion of a finger having a cured artificial nail structure coupled to a portion of a fingernail in accordance with an embodiment of the invention.

The procedure may be repeated on all fingernails of, for example, one hand before the coating of the composition on each fingernail is exposed to actinic radiation 140 such as visible light or UV light as shown in FIG. 4. The sample cures (e.g., polymerizes) in one embodiment in about 5 minutes. Once the composition cures, form 120 is removed and the formation of the artificial nail structure is complete as shown in FIG. 5.

The invention allows for the application of the composition on multiple fingernails prior to curing the composition of any one nail. The multiple applications may be achieved with the composition on each fingernail maintaining its shape (e.g., minimal sagging). Minimal or insubstantial sagging means that when cured, the artificial nail structure does not require significant filing to be formed into the desired shape. Instead, the desired shape is formed prior to curing and remains in such state after curing.

The invention also does not experience discoloration as experienced in prior art catalyzed artificial nail structures. The reduction in sagging over prior art compositions is believed to be the result of the inclusion of the thixotrope, e.g., 'Salcare SC 95' or 'Salcare SC 96'. Secondary bonding associations between the polar urethane linkages and the thixotrope helps to form a 3-dimensional network structure which prevents sagging and dripping before the coat is cured. The thixotrope provides a lower viscosity at high shear rate and fast yield point recovery for better pattern definition. Fumed silica by itself fails to form a three dimensional network essential to prevent sagging.

The following examples of photopolymeric compositions are given below:

| Ingredient | Weight Percent |
|---|---|
| Example 1 | |
| Acrylated Aliphatic Urethane Oligomer | 61 |
| TEDMA | 26 |
| Darocur 1173 | 2.9 |
| Salcare SC 96 | 6 |
| Fumed Silica | 4 |
| Titanium Dioxide | 0.1 |
| MEHQ | 100 ppm |
| Example 2 | |
| Acrylated Aliphatic Urethane Oligomer | 40 |
| TEDMA | 27 |
| Darocur ll73 | 3.1 |
| Salcare SC 96 | 7.3 |
| Fumed Silica | 3.6 |
| Hydroxyethyl Methacrylate | 19 |
| BHT | 150 ppm |
| Example 3 | |
| Acrylated Aliphatic Urethane Oligomer | 40 |
| EDMA | 22 |

-continued

| Ingredient | Weight Percent |
|---|---|
| Darocur 1173 | 3.5 |
| Salcare SC 96 | 8.5 |
| Isobornyl Acrylate | 11 |
| Hydroxyethyl Methacrylate | 15 |
| MEHQ | 75 ppm |
| Example 4 | |
| Acrylated Aliphatic Urethane Oligomer | 40 |
| EDMA | 22 |
| Darocur 1173 | 3.5 |
| Salcare SC 95 | 5.0 |
| Isobornyl Acrylate | 11 |
| Hydroxyethyl Methacrylate | 15 |
| Fumed Silica | 3.5 |
| BHT | 50 ppm |
| MEHQ | 60 ppm |
| Example 5 | |
| Acrylated Aliphatic Urethane Oligomer | 45 |
| EDMA | 26 |
| Diethoxyacetophenone | 1 |
| Benzoin | 2.5 |
| Salcare SC 95 | 5.0 |
| Hydroxypropyl Methacrylate | 6 |
| Hydroxyethyl Methacrylate | 10 |
| Fumed Silica | 4.5 |
| MEHQ | 95 ppm |
| Example 6 | |
| Acrylated Aliphatic Urethane Oligomer | 45 |
| EDMA | 26.5 |
| Titanium Dioxide | 0.5 |
| Camphorquinone | 2.5 |
| Salcare SC 95 | 5.0 |
| Hydroxypropyl Methacrylate | 7 |
| DMAEM | 9 |
| Fumed Silica | 4.5 |
| MEHQ | 120 ppm |
| Example 7 | |
| Acrylated Aliphatic Urethane Oligomer | 45 |
| TEDMA | 20 |
| MOEOEMA | 6.5 |
| Camphorquinone | 2.5 |
| Salcare SC 96 | 5.0 |
| Hydroxypropyl Methacrylate | 7 |
| DEAEM | 9 |
| Fumed Silica | 4.5 |
| MEHQ | 80 ppm |
| Example 8 | |
| Acrylated Aliphatic Urethane Oligomer | 40 |
| EDMA | 22 |
| Darocur 1173 | 3.5 |
| Salcare SC 96 | 8.5 |
| Isobornyl Acrylate | 6 |
| Ethyl Methacrylate | 20 |
| MEHQ | 75 ppm |
| Example 9 | |

The following presents a formulation procedure for making an embodiment of the photopolymerizable thixotropic composition of the invention.

(1) The composition should be formulated either under yellow or red light.
(2) Blend the aliphatic acrylated urethane oligomer with cross-linker(s) and/or monomers.
(3) Weigh the blend in a steel vessel fitted with a stirrer and disperser. The vessel must be connected to a vacuum pump. To the blend add photoinitiator, thixotrope and auxillaries such as inhibitor and/or pigments.
(4) Begin stirring the composition with a stirrer. At the same time, start the vacuum pump and open the valve leading to the vessel. As air is drawn out, the level of liquid composition rises. Shut off the valve and allow the contents of the vessel to adjust to its new reduced pressure. The level begins dropping as the composition adjusts to the new pressure. After the composition

| Ingredient | Weight Percent |
|---|---|
| has adjusted to the new reduced pressure and the level has dropped, open the valve to the vacuum. Repeat this procedure until the pressure in the vessel reads about 0 mm Hg. The reduced pressure removes air that was trapped within the composition. | |
| (5) Start a disperser for about 5 minutes to ensure removal of last traces of air. | |
| (6) Shut off the disperser, stirrer and vacuum pump. Slowly release in the air. | |

The composition should sit overnight before filling commences in yellow or red light.

In the preceding detailed description, the invention is described with reference to specific exemplary embodiments thereof. Further, the description made reference to commercially available components for use in embodiments of the invention. It will, however, be evident to those of ordinary skill in the art that various modifications and changes may be made thereto without departing from the broader spirit and scope of the invention as set forth in the claims. The specification is to be regarded in an illustrative rather than a restrictive sense.

The embodiments of the invention in which an exclusive property or privilege is claimed are defined as follows:

1. A composition comprising:
   one of an acrylic aliphatic urethane oligomer and a substituted acrylic aliphatic urethane oligomer;
   a cross-linker;
   a thixotropic emulsion comprising polyquaternium 37, propylene glycol dicaprylate/dicaprate, and PPG-1 trideceth-6; and
   an initiator,
   wherein the composition is adapted to be formed into a coating on a portion of a natural nail and the coating maintains its formation prior to curing.

2. The composition of claim 1, wherein the initiator is a photoinitiator.

3. The composition of claim 1, wherein the thixotropic emulsion is present in an amount comprising 0.5 percent to 10 percent by weight of the total weight of the composition.

4. The composition of claim 3, wherein the thixotropic emulsion further comprises fumed silica.

5. The composition of claim 2, further comprising a monomer in an amount comprising 20 percent to 70 percent by weight of the total weight of the composition.

6. The composition of claim 2, wherein the cross-linker is present in an amount comprising up to 50 percent of the total weight of the composition.

7. The composition of claim 2, wherein the urethane oligomer is present in an amount comprising 20 percent to 80 percent by weight of the total composition.

8. A method comprising:
   applying to a substrate of a human nail a composition comprising:
      one of an acrylic aliphatic urethane oligomer and a substituted acrylic aliphatic urethane oligomer;
      a cross-linker;
      a thixotropic emulsion; and
      an initiator,
   sculpting the composition into a desired form; and
   curing the composition.

9. The method of claim 8, wherein the curing comprises exposing the composition to actinic radiation.

10. The method of claim 9, wherein the actinic radiation comprises one of visible and ultraviolet radiation.

11. The method of claim 8, wherein the substrate is a portion of a natural nail and a portion of an artificial nail.

* * * * *